United States Patent [19]

Klein

[11] 4,305,936

[45] Dec. 15, 1981

[54] TOPICAL CORTICOSTEROID FORMULATIONS

[75] Inventor: Robert W. Klein, Blue Bell, Pa.

[73] Assignee: Dermik Laboratories, Fort Washington, Pa.

[21] Appl. No.: 195,706

[22] Filed: Oct. 9, 1980

[51] Int. Cl.$^3$ .............................................. A61K 31/56
[52] U.S. Cl. .................................. 424/242; 424/243; 424/238
[58] Field of Search ................ 424/238, 242, 243, 241

[56] References Cited

U.S. PATENT DOCUMENTS 3,862,311  1/1975  Leeson ................................ 424/238
3,991,203  11/1976  Rajadhyaksha ..................... 424/238
4,048,309  9/1977  Chen et al. .......................... 424/238

*Primary Examiner*—Elbert L. Roberts
*Attorney, Agent, or Firm*—Austin R. Miller; John Lezdey; James A. Nicholson

[57] ABSTRACT

This present invention relates to a solution for topical or local application comprising at least one corticosteroid; from about 1% to 4% by weight of solubilization agents consisting essentially of a combination of at least one glyceryl ester of a fatty acid of 6 to 22 carbon atoms and a betaine surfactant, from about 10% to 50% by weight of composition of an alkanol cosolvent, and from about 20% to 50% water.

9 Claims, No Drawings

TOPICAL CORTICOSTEROID FORMULATIONS

BACKGROUND OF THE INVENTION

This invention relates to vehicles for topical or local application of corticosteroids and to mixtures of the vehicle and medicaments. In particular, this invention relates to new, improved medicament vehicles having advantages over previously known vehicles.

One of the oldest types of medicament vehicles is the ointment, a preparation containing active medications that can be readily applied and rubbed into the skin. It serves as a means for distributing the medication uniformly over the skin surface and maintaining it there until beneficial action can occur. The earliest ointment preparations were based on fats, waxes, greases and petrolatum. These are, by nature, greasy or not water-washable and have a limited ability to release medication to the skin. A non-aqueous ointment of more recent origin is a mixture of polyethylene glycols having molecular weights of 1,000 to 20,000. This vehicle, although water-washable, has a greasy texture and does not provide an occlusive dressing on a treated surface.

Topical corticosteroid formulations are extensively employed in the treatment of skin disorders, such as dermatitis. To be therapeutically effective, the active ingredient must be in a molecular dispersion to facilitate desired percutaneous absorption which is particularly important is achieving a therapeutic response for the management of psoriasis. Unfortunately, the more effective corticosteroids are essentially insoluble in water (less than 0.0005% soluble), hydrocarbon vehicles such as mineral oil, petrolatum, and polyethylene gelled mineral oil. Various organic solvents and solubilizers have been found to be good solvents for such steroid. However, they have been found to be unsuitable for commercial application for reasons such as their high volatility and low boiling points, their disagreeable odor, their "paint removing" property, and their undesirable skin reaction. Furthermore, various water-soluble emulsifiers and oily liquids or emollients have been suggested for use in preparing creams or lotions. However, because of the undesirably low solubility of the corticosteroid in such vehicles, higher levels of these materials in topical products are required thereby increasing their cost, increasing the risk of irritation and also adversely affecting their cosmetic elegance.

By local application it is meant use in body cavities including mucous membranes, i.e., vaginal, nasal, anal, etc. and in the treatment of inflammation and irritations which occur, including vaginitis, hemorrhoids and the like. Accordingly, in view of the above considerations, it is seen that a need exists for a suitable vehicle capable of solubilizing a sufficient amount of the corticosteroid so that it may be employed in topical or local formulations, while being dermatologically beneficial, stable, and pharmaceutically acceptable.

It is accordingly the purpose of this invention to provide an essentially water-washable base which provides an occlusive film for longer and better therapeutical activity; release the medicaments more quickly and effectively; bring dissolved therapeutic agent in known dilution in contact with the skin; spread evenly and adhere well even if the skin is moist; be readily removed from the skin or fabrics with water; serve as an excellent levigating material for many prescribed ingredients that usually require separate treatment before being incorporated into one of the bases; and because it does not hydrolyze, deteriorate, become rancid, support mold growth or require preservatives.

It is a further object of this invention to provide a vehicle using a unique system, new for topical or local preparations, which has exceptional solubilizing properties particularly for corticosteroids.

It is a still further object of the present invention to provide a new topical or local preparation which can produce a foam when packaged either in the form of an aerosol or a non-aerosol foam-forming closure system.

SUMMARY OF THE INVENTION

The composition of the present invention comprises:

(a) from about 1% to 4% by weight of solubilization agents consisting essentially of a combination of a glyceryl ester of a fatty acid of 6 to 22 carbon atoms and a betaine surfactant, preferably in the amounts of 1% to 3%, by weight of the corticosteroid of glyceryl ester and about 0.4-% by weight of corticosteroid of betaine surfactants.

(b) from about 10% to about 50% by weight of the entire formulation of an alkanol-glycol cosolvent; and (c) about 0.005% to about 2.0% by weight, and preferably from about 0.025% to about 1% based on the total weight of the composition, of a corticosteroid.

The glyceryl esters of fatty acids of 6 to 22 carbon atoms, particularly those having melting points in the range of about −20° C. to 80° C. have been found to be most suitable. Typical representative examples of the glyceryl esters include the following:

glyceryl stearate,
glyceryl palmitate,
glyceryl laurate,
glyceryl cocoate,
glyceryl capric/caprylic ester
glyceryl oleate,
glyceryl distearate,
glyceryl dipalmitate,
glyceryl dilaurate,
glyceryl stearate laurate,
glyceryl tristearate,
glyceryl tripalmitate,
glyceryl trilaurate,
glyceryl trimyristate,
glyceryl tricocate,
glyceryl trihydrogenated cocate,
glyceryl tricaprylate,
glyceryl trioleate,
and the like.

Especially good results have been obtained utilizing PEG-7 glyceryl cocoate (Standamul HE) and cocamidopropyl betaine (Lexaine C) in combination.

As will be seen hereinafter, other active ingredients may be employed in conjunction with the corticosteroid. In such case, the other active ingredients, such as iconysol, nystatin, neomycins, gramicydins and the like, or mixtures thereof, may be employed in amounts up to 2% or more. The topical steroid formulations of the present invention may take the form of a lotion or cream, that is, those formulations which include a relatively large aqueous phase and a relatively small oil phase. Suitable glycol cosolvents used in the present composition include 1,2-propane diols, 1,3-propane diol, polyethylene glycol having a molecular weight of from 100 to 800, dipropylene glycol, and the like or mixtures thereof. The lower alkanol cosolvent is preferably ethanol.

The composition of this invention also contains a stabilizing amount of a surfactant, that is, an amount sufficient to maintain homogeneity of the other ingredients. The particular concentration will vary depending upon the choice of surfactant and the selection of the other ingredients. In general, stabilizing amounts can be as low as 0.1% or lower. In some instances as high as 10% or higher of surfactant may be desired. Generally from 2% to 5% is suitable. The amount of surfactant should be the minimum required for stability. Suitable surfactants include pharmaceutically acceptable, non-toxic, non-ionic, anionic and cationic surfactants. Examples of suitable non-ionic surfactants include glycerol fatty acid esters such as glycerol monostearate, glycol fatty acid esters such as propylene glycol monostearate, polyhydric alcohol fatty acid esters such as polyethylene glycol (400) monooleate, polyoxyethylene fatty acid esters such as polyoxyethylene (40) stearate, polyoxyethylen fatty alcohol ethers such as polyoxyethylene (20) stearyl ether, polyoxyethylene sorbitan fatty acid esters such as polyoxyethylene sorbitan monostearate, fatty acid ethanolamides and their derivatives such as the diethanolamide of stearic acid, and the like. Examples of suitable anionic surfactants are soaps including alkali soaps, such as sodium, potassium and ammonium salts of aliphatic carboxylic acids, usually fatty acids, such as sodium stearate. Organic amine soaps, also included, include organic amine salts of aliphatic carboxylic acids, usually fatty acids, such as sodium stearate. Organic amine soaps, also included, include organic amine salts of aliphatic carboxylic acids, usually fatty acids, such as triethanolamine stearate. Another class of suitable soaps is the metallic soaps, salts of polyvalent metals and aliphatic carboxylic acids, usually fatty acids, such as aluminum stearate. Other classes of suitable anionic surfactants include sulfated fatty acid alcohols such as sodium lauryl sulfate, sulfated oils such as the sulfuric ester of ricinoleic acid disodium salt, and sulfonated compounds such as alkyl sulfonates including sodium cetane sulfonate, amide sulfonates such as sodium cetane sulfonate, amide sulfonates such as sodium N-methyl-N-oleyl laurate, sulfonated dibasic acid esters such as sodium dioctyl sulfosuccinate, alkyl aryl sulfonates such as sodium dodecylbenzene sulfonate, alkyl naphthalene sulfonates such as sodium isopropyl naphthalene sulfonate, petroleum sulfonate such as aryl naphthalene with alkyl substitutes. Examples of suitable cationic surfactants include amine salts such as octadecyl ammonium chloride, quarternary ammonium compounds such as benzalkonium chloride. Other examples of these and other suitable surfactants can be found in "Pharmaceutical Emulsions and Emulsifying Agents" by Lawrence M. Spatton, second edition; The Chemist and Druggist, London; "Emulsions' Theory and Practice" by Paul Becher, Reinhold Publishing Corporation, New York; and "Detergents and Emulsifyers, 1969 Annual" by John M. McCutcheon, Morristown, N.J., the disclosures thereof being incorporated herein by reference.

The composition of this invention can also contain from 0% to 15%, and preferably from 0.1% to 5% of a compatible plasticizer. Suitable compatible plasticizers include carboxylic vinyl polymers (Carbopols ®), polyethylene glycol having a molecular weight of from above 800 to 20,000; natural gums including acacia gum, guar gum, karaya, tragacanth, and the like; seaweed products such as agar, irish moss and alginates; cellulose, plus derivatives such as sodium carboxymethyl cellulose and the like; starch, starch derivatives and dextrins; pectin and pectates; saponins; and water soluble or water dispersible vinyl polymers such as polyvinylpyrrolidone, polyvinyl alcohol, vinyl pyrrolidonevinyl alcohol copolymers, and the like. The plasticizer maintains homogeneity in the mixture at ambient temperatures, that is, temperatures at which the fatty alcohol is solid. This component also improves the plasticity, and uniformity of the medicament mixtures with the vehicle and provides to the vehicle smoothness and a more pleasing "feel"; hence, the vehicle containing the plasticizer is cosmetically acceptable.

It should be understood that the medicament vehicles of this invention can also contain other non-essential ingredients. The vehicle can contain up to 10 weight percent of conventional pharmaceutical adjuvants. These adjuvants or additives are used to improve consistency, emolliency, homogeneity, spreadability, texture and appearance of the vehicle or its residual film or the stability of the medicament. They can be used to give a residual film, varying degrees of continually, flexibility, adhesion, occlusion, water repellancy, washability, and the like. Suitable auxiliary adjuvants include hydrocarbons ranging from liquid petrolatum to solid paraffins and waxes, beeswax, saturated fatty acids having from 16 to 24 carbons such as stearic acid, palmitic acid, benhenic acid; fatty acid amides such as oleamide, palmitamide, stearamide, behenamide; and esters of fatty acids having from 14 to 24 carbons such as isopropyl myristate sorbitan monostearate, polyethylene glycol mono- and di stearates, propylene glycol monostearate isostearyl neopentanoate, and the corresponding mono and diesters of other fatty acids such as oleic and acid and palmitic acid. It is preferable that the fatty acids be saturated and the fatty acids and amides be substantially free from irritating amounts of acids or amides having fewer than 14 carbons. Other optional adjuvants include miscellaneous natural products such as wool fat, wool alcohol. cholesterol and its derivatives, lecithin and proteins such as gelatin, casein, soyabean protein, egg albumen. Finely dispersed mineral solids useful as thickeners include colloidal clays such as bentonite and polyvalent metal hydroxides such as magnesium hydroxide. Suitable chemical stabilizers include citric acid, sodium citrate and other agents to adjust pH, ethylenediamine tetraacetic acid and its salts and other chelating or sequestering agents, propyl gallate, butylated hydroxy anisole or toluene, and other antioxidants.

A vehicle of the present invention may be used for any of the known effective anti-inflammatory corticosteroids. Among the suitable corticosteroids there may be included:
hydrocortisone,
hydrocortisone acetate,
hydrocortisone butyrate,
hydrocortisone valerate,
triamcinolone acetonide,
fluocinolone acetonide,
16α-hydroxy prednisolone-16α, 17-acetonide,
fluohydrocortisone,
1-dehydroxycortisone,
β-methasone,
9α,11β-dicloro-6α-fluoro-21-hydroxy-16α,17α-isopropylidenedioxypregna-1, 4-diene-3,20-dione,
9α-fluoro-11β,17α-21-trihydroxy-16β-methylpregna-1, 4-diene-3,20-dione, 9α-fluoro-11β, 21-dihydroxy-16β-methyl-17α-valeroxy-pregna-1,4-diene-3,20-dione,
17α,21-dihydroxypregn-4-ene-3,11,20-trione,
17α-hydroxy-21-acetoxypregn-4-ene-3,11,20-trione,
21-hydroxypregn-4-ene-3, 20-dione,
21-acetoxypregn-4-ene-3, 20-dione,
21-divaloxypregn-4-ene-3, 2-dione,
9α-fluoro-11β, 17α,21-trihydroxy-16α-methylpregna-1,4-diene-3, 20-dione,
6α,9β-difluoro-11β, 17α-dihydroxypregna-1,4-diene-3, 20-dione,
6α-fluoro-11β,21-dihydroxy-16α-17α-isopropylidenedioxypregn-4-ene-3, 20-dione,
11β,17α-dihydroxy-21-acetoxypregna-4-ene-3, 20-dione,
6α-methyl-11β,17α,21-trihydroxypregna-1,4-diene-3, 20-dione,
6α-methyl-11β,17α-dihydroxy-21-acetoxy-pregna-1,4-diene-3, 20-dione,
6α-fluoro-11β,17α,21-trihydroxy-16α-methylpregna-1, 4-diene-3, 20-dione,
6α-fluoro-11β,17α-dihydroxy-16α-methyl-21-acetoxy-pregna-1,4-diene-3, 20-dione,
6α-fluoro-11β,hydroxy-16α,17α-isopropylidenedioxy-21-acetoxypregna-1,4-diene-3,20-dione,
11β,17α,21-trihydroxypregna-1,4-diene-3,20-dione,
11β,17α-dihydroxy-21-acetoxypregna-1,4-diene-3, 20-dione,
17α,21-dihydroxypregna-1,4-diene-3,11,20-trione,
17α,hydroxy-21-acetoxypregna-1,4-diene-3-11,20-trione,
9α-fluoro-11β,16β,17α,21-tetrahydroxypregna-1,4-diene-3, 20-dione,
9α-fluoro-11β,16α,17α-trihydroxy-21-acetoxypregna-1,4-diene-3, 20-dione,
6α,9α-difluoro-11β,21-dihydroxy-16α-methyl-17α-valeroxypregna-1,4-diene-3, 20-dione,
6α,9α-difluoro-11β,17α,21-trihydroxy-16α-methyl pregna-1,4-diene-3, 20-dione,
6α,7α-difluoromethylene-11β,17α,21-trihydroxy-pregna-4-ene-3, 20-dione,
6α,9α-difluoro-11β-hydroxy-16α,17α-isopropylidenedioxy-21-chloropregna-1,4-diene-3, 20-dione,
9α,11β-dichloro-6α,21-difluoro-16α,17α-isopropylidenedioxypregna-1,4-diene-3,20-dione, and
9α,11β,21-trichloro-6α-fluoro-16α,17α-isopropylidenedioxypregna-1,4-diene-3, 20-dione.

The medicaments can be incorporated into the base of the present invention by conventional techniques. A bulky, insoluble powder should be mixed beforehand with a small portion of the base mixture propylene glycol-alcohol, and then blended with the remainder of the base. Heat sensitive medicaments (in particular, some antibiotics) can be dissolved or suspended in a small amount of glycol-alcohol cosolvent or other liquid, and then mixed with the vehicle during or after its preparation.

The amount of medicament to be incorporated into the base will, of course, depend upon the type of medicament and its intended use; the determination of suitable medicament concentrations is a matter of routine fully within the conventional scope of the art. In general, therapeutically effective amounts of the medicament are incorporated into the vehicle.

The term "topical" as employed here relates to the external use of the medicament, incorporated into the present vehicle, at the site of the inflammation. Accordingly, the composition of this invention includes pharmaceutical forms in which the medicament is applied externally for direct contact with the surface to be treated. Conventional pharmaceutical forms for this purpose include ointments, creams, lotions, solutions, suspensions, pastes, jellies, sprays, and aerosols, suppositories and the like for use on the skin and the like. Propellants for use in preparing the aerosols of the present invention include, for example, liquified gases such as trichlorofluoromethane, dichlorofluoromethane, chloropentafluorethane, propane, n-butane, and gases such as nitrogen and carbon dioxide.

The following examples will further illustrate the formulations of this invention but are not to be considered as limiting the scope of this invention.

EXAMPLE 1

A clear liquid preparation was formed from the following formulation:

| Ingredient | Weight % |
|---|---|
| Phase I | |
| Standamul HE, DF (PEG-7 Glyceryl Cocoate | 2.00 |
| Lexaine C (Cocamidopropyl betaine) | 2.00 |
| Iso-Stearyl Neo Pentanoate | 0.05 |
| Isopropyl Myristate, NF | 0.05 |
| Polyethylene Glycol 400 Diisostearate | 0.05 |
| Phase II | |
| Propylene Glycol, USP | 15.00 |
| S.D. Alcohol #40-B/190°, Df | 29.00 |
| Hydrocortisone, USP | 0.550 |
| Phase III | |
| Purified Water, USP | 50.255 |
| Catamer Q* | 1.00 |
| Citric Acid, USP | 0.010 |
| Sodium Citrate, USP | 0.035 |

*Copolymer of acrylamide and Trimethyl ammonium ethyl methacrylate methosulfate [CTFA name is: Polyquaternium 3].

Phase I, II and Phase III were mixed separately to achieve respective solutions. Thereafter, Phase I was added slowly with vigorous stirring to Phase II. The mixture was stirred and Phase III was added thereto with stirring. The resulting solution was mixed to homogeneity. This solution can be dispensed as a non-aerosol foam utilizing conventional plastic bottles and non-aerosol foam devices, such as those supplied by companies including Cosval, AFA/Thiokol Co., and Glassrock Co.

The solution may also be impregnated into a tampon for vaginal use in treating local inflammation.

EXAMPLE II

Nine parts by weight of the solution of Example I was combined with 1 part by weight of a propellant (40-dichloro-difluoro-methane/60-dichlorotetrafluorethane) under pressure in suitable aerosol container equipped with conventional valve apparatus and foam-foaming head.

The foam preparation is used in the treatment of the majority of steroid-responsive dermatoses using either the open or occlusive method of drug application.

A small amount of the foam is applied to the affected skin area one-to-three times a day as needed for treatment of atopic dermatitis, neurodermatitis, contact dermatitits, seborrheic dermatitis, eczematous dermatitis, puritis ani, intertrigo, intertrigenous psoriasis and the like. The quantity of corticosteroid in the formulation may be increased up to 2½% w/w in order to achieve a higher potency formulation.

EXAMPLE III

The following ingredients were formulated into a cream:

| Weight % | Ingredients |
| --- | --- |
| 0.025 | 6α,9α-difluoro-11β,17α,21-tri-hydroxy-6β-methylpregna-1,4-diene-3, 20-dione, 17,21-diacetate |
| 2.00 | Standamul HE, DF |
| 2.00 | Lexaine C |
| 10.00 | Stearic acid |
| 5.2 | Sorbitan monostearate |
| 1.0 | Sorbitan monooleate |
| 0.01 | Citric acid |
| 0.20 | Sorbic acid |
| 5.0 | Propylene glycol |
| 5.0 | Ethanol |

Distilled water to produce 100 parts by weight.

A mixture of the stearic acid, sorbitan monooleate, sorbitan monostearate, Lexaine C and Standamul were heated to 60° C. to 65° C. and added to a stirred solution containing citric acid and sorbic acid dissolved in the water at 60° C. to 65° C. The mixture was stirred at 60° C. to 65° C., then cooled to 50° C.; the steroid in the propylene glycol and ethanol is added and stirred while cooling the cream to 35° C.

As a complimentary active ingredient, sterilized neomycin sulfate can be added in an amount to provide a final concentration of 0.5 percent by weight.

The cream is used in the treatment of the majority of corticosteroid-responsive dermatoses using either the open (without occlusion) or occlusive method of drug application.

The quantity of steroid in this example can be increased to either about 0.2% w/w to achieve a higher potency cream or decreased to 0.01% or 0.001% w/w to achieve a lower potency maintenance cream.

What is claimed is:

1. A composition useful as a vehicle for corticosteroids for topical or local applications comprising; from about 1% to 4% by weight of solubilization agents consisting essentially of a combination of at least one glyceryl ester of a fatty acid of 6 to 22 carbon atoms and cocamidopropyl betaine, from about 10% to 50% by weight of composition of an alkanolglycol cosolvent and from about 10% to 50% water.

2. The composition according to claim 1 wherein said corticosteroid is present in an amount of about 0.005% to about 2.5% by weight of composition.

3. The composition according to claim 1 wherein said glyceryl ester is glycereth-7-cocoate.

4. The composition according to claim 1 wherein said corticosteroid is selected from the group consisting of hydrocortisone, hydrocortisone acetate, betamethasone and triamcinolone acetonide.

5. The composition according to claim 1 including a further surfactant.

6. The composition according to claim 1 in aerosol form.

7. The composition according to claim 1 including a plasticizer.

8. An aqueous foamable composition useful as a vehicle for a corticosteroid comprising:
 (a) from about 1% to 4% by weight of composition of glycereth-7-cocoate and cocamidopropyl betaine;
 (b) from about 10% to about 50% by weight of composition of an alkanol-glycol cosolvent; and
 (c) water.

9. The composition according to claim 8 wherein said corticosteroid is selected from the group consisting of hydrocortisone, hydrocortisone acetate, betamethasone and triamcinolone acetonide.

* * * * *